US00PP07945P

United States Patent [19]

Warriner

[11] Patent Number: Plant 7,945

[45] Date of Patent: Aug. 18, 1992

[54] ROSE PLANT JACSMELL

[75] Inventor: William A. Warriner, Tustin, Calif.

[73] Assignee: Bear Creek Gardens, Inc., Medford, Oreg.

[21] Appl. No.: 625,873

[22] Filed: Dec. 10, 1990

[51] Int. Cl.[5] ..... A01H 5/00

[52] U.S. Cl. ..... Plt./18

[58] Field of Search ..... Plt./11, 18, 19, 20

*Primary Examiner*—Howard J. Locker

*Attorney, Agent, or Firm*—Klarquist, Sparkman, Campbell, Leigh and Whinston

[57] ABSTRACT

A hybrid tea class rose plant having very strong fragrance, long bud, large open flowers, and thick, leathery petals.

1 Drawing Sheet

The present invention relates to a new and distinct variety of rose plant of the hybrid tea class which was originated by me by crossing the variety Jadis, U.S. Plant Pat. No. 3,423, with the variety First Prize, U.S. Plant Pat. No. 2,774.

The primary objective of this breeding was to produce a new rose variety having the strong fragrance of Jadis coupled with the heavy petal substance and very large flower size of First Prize. The objective was substantially achieved along with other desirable improvements as evidenced by the following unique combination of characteristics which are outstanding in the new variety and which distinguish it from its parents, as well as from all other varieties of which I am aware:

1. Very strong fragrance.
2. Very long bud.
3. Very large open flower.
4. Thick leathery petals.

Asexual reproduction of this new variety by budding, as performed at Wasco, Calif., shows that the foregoing characteristics and distinctions come true to form and are established and transmitted through succeeding propagations.

The accompanying illustration shows typical specimens of the vegetative growth and flowers of this new variety in different stages of development, depicted in color as nearly true as it is reasonably possible to make the same in a color illustration of this character.

The following is a detailed description of my new rose cultivar with color description using terminology in accordance with The Royal Horticultural Society (London) Colour Chart, except where ordinary dictionary significance of color is indicated.

Parentage:

*Seed parent.*—Jadis, U.S. Plant Pat. No. 3,423.

*Pollen parent.*—First Prize, U.S. Plant Pat. No. 2,774.

Classification:

*Botanical.*—*Rosa hybrida.*

*Commercial.*—Hybrid tea.

FLOWER

Observations made from specimens grown in a garden in Somis, Calif. in Sep., 1990.

Blooming habit: Recurrent.

Bud:

*Size.*—2 to 2½ inches when the petals start to unfurl.

*Form.*—Very long, pointed ovoid.

*Color.*—When sepals first divide, bud color is Red Group 55A. When half blown, the upper sides of the petals are Red Group 55B; and the lower sides of the petals are Red Group 55B.

*Sepals.*—Color: Green Group 138C. Surface texture: Covered with fine hairs. There are three normally to occasionally heavily appendaged sepals. There are two unappendaged sepals with hairy edges.

*Receptacle.*—Color: Green Group 138C. Shape: Funnel. Size: Medium (⅜"×⅜"). Surface: Smooth.

*Peduncle.*—Length: Medium (3"). Surface: Glandular. Color: Light Green. Strength: Stiff, erect, heavy.

Bloom:

*Size.*—Very large. Average open size is 5 to 6".

*Borne.*—Singly.

*Stems.*—Long (18"), strong.

*Form.*—When first open: High center. Permanence: Retains its form to the end, outer petals curl back.

*Petalage.*—Number of petals under normal condition: 30.

*Color.*—The upper side of the petals is Red Group 55B. The reverse side of the petals is Red Group 55B. The base of each petal has a Yellow half moon at the point of attachment (¼"×¼"). The major color on the upper side is Red Group 55B.

*Variegations.*—None.

*Discoloration.*—No change in the general tonality at the end of the first day, at the end of the third day, generally fades from Red 55B to 55C to 55D.

*Fragrance.*—Strong.

Petals:

*Texture.*—Thick, leathery.

*Shape.*—Round.

*Form.*—Tips slightly recurved, edges slightly quilled.

*Arrangement.*—Imbricated. Petaloids in the center: Few.

*Persistence.*—Drop off cleanly.

*Lastingness.*—On the plant: Fair, 5 days. As a cut flower: Long, 5 to 7 days.

Reproductive parts:

*Anthers.*—Size: Large. Quantity: Many. Color: Yellow. Arrangement: Regular around styles.

*Filaments.*—Color: Reddish brown.

*Pollen.*—Color: Lemon yellow.

*Styles.*—Color: Reddish.

*Stigmas.*—Color: Greenish white.

Form: Bush.

Growth: Vigorous, upright, branching.

Foliage:

*Number of leaflets on normal mid-stem leaves.*—5 or 7.

*Size.*—Large (5½"×4").

*Quantity.*—Normal.

*Color.*—New foliage: Reddish green. Old foliage: Medium to dark green.

Leaflets:

*Shape.*—Pointed oval.

*Texture.*—Upper side: Smooth.

*Edge.*—Serrated.

*Serration.*—Single.

*Petiole rachis.*—Color: Reddish becoming green with age.

*Petiole underside.*—Rough with prickles and glands.

*Stipules.*—Short (½"), edged with glands.

*Disease resistance.*—Susceptible to mildew and blackspot under normal growing conditions at Somis, Calif.

Wood:

*New wood.*—Color: Light green. Bark: Smooth.

*Old wood.*—Color: Green. Bark; Smooth.

Prickles:

*Quantity.*—On main canes from base: Ordinary. On laterals from main canes: Ordinary.

*Form.*—Straight to hooked slightly downward.

*Color when young.*—Red.

Small prickles:

*Quantity.*—On main stalks: Few. On laterals: Many.

*Color.*—Brown.

I claim:

1. A new and distinct variety of rose plant of the hybrid tea class, substantially as herein shown and described, characterized particularly as to novelty by the unique combination of its very strong fragrance, long bud, large open flower, and thick leathery petals.

* * * * *

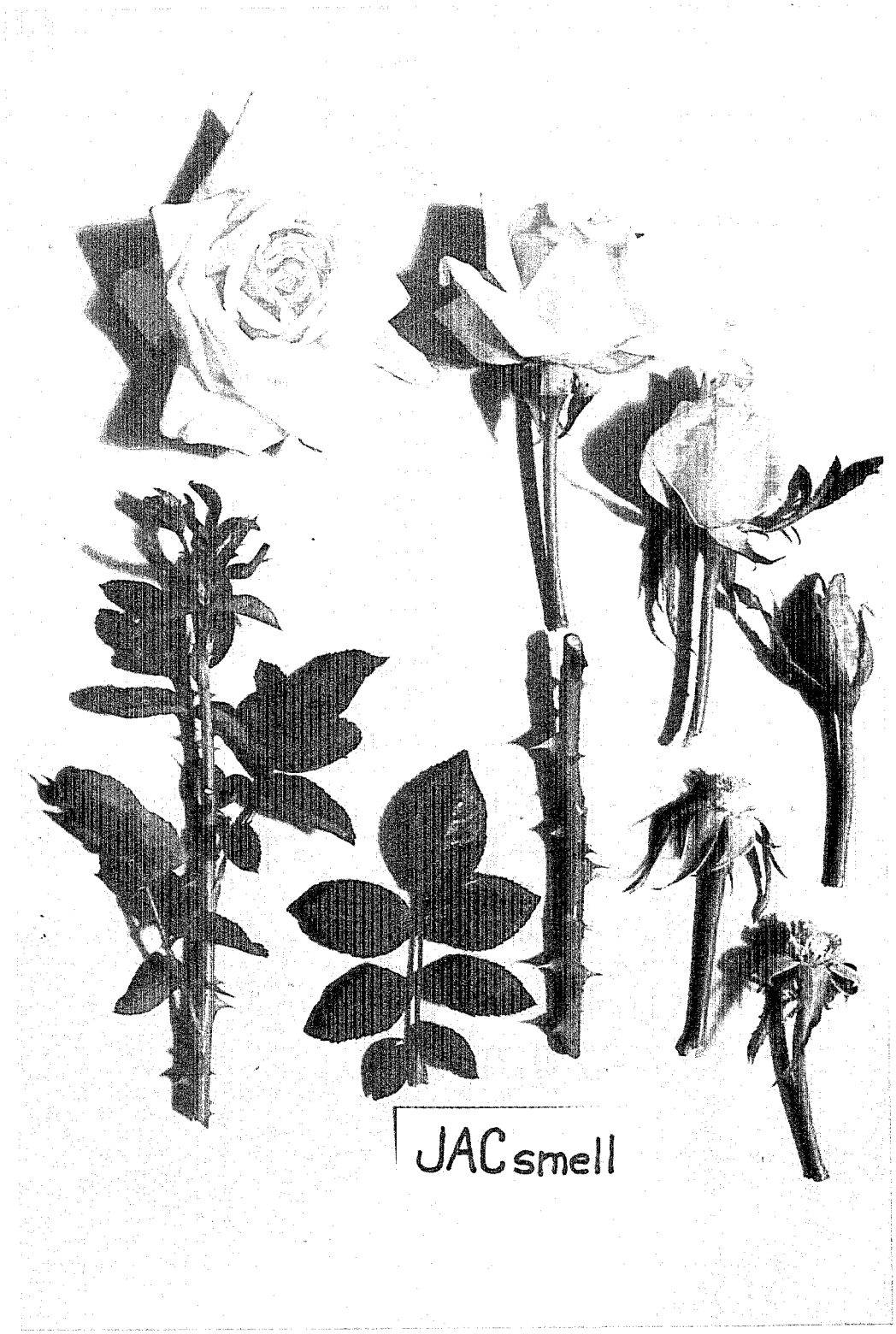
JAC smell